United States Patent [19]

Huber, Jr. et al.

[11] Patent Number: 5,099,064

[45] Date of Patent: Mar. 24, 1992

[54] METHOD FOR INCREASING CONVERSION EFFICIENCY FOR OXIDATION OF AN ALKYL AROMATIC COMPOUND TO AN AROMATIC CARBOXYLIC ACID

[75] Inventors: William F. Huber, Jr.; Martin A. Zeitlin, both of Naperville, Ill.

[73] Assignee: Amoco Corporation, Chicago, Ill.

[21] Appl. No.: 814,655

[22] Filed: Dec. 30, 1985

[51] Int. Cl.$^5$ ................. C07C 51/265; C07C 59/84
[52] U.S. Cl. ............................................. 562/414
[58] Field of Search ....................................... 562/414

[56] References Cited

U.S. PATENT DOCUMENTS

| | | | |
|---|---|---|---|
| 2,788,367 | 4/1957 | Bills et al. | 562/414 |
| 2,906,775 | 9/1959 | Taplin | 562/414 |
| 3,928,433 | 12/1975 | Onopchenko et al. | 562/414 |
| 3,970,696 | 7/1976 | Shigeyasu et al. | 562/414 |

FOREIGN PATENT DOCUMENTS 1262259  3/1968  Fed. Rep. of Germany ...... 562/414

*Primary Examiner*—Vivian Garner
*Attorney, Agent, or Firm*—James R. Henes; William H. Magidson; Ralph C. Medhurst

[57] ABSTRACT

A method and system for increasing conversion efficiency of aromatic alkyl reactant to aromatic carboxylic acid product and for improving the quality of the product, are disclosed. The method and system provide for the continuous production of an aromatic carboxylic acid by the liquid phase, exothermic oxidation of an aromatic alkyl in a vaporizable solvent in an oxidation reactor. The reactor makes use of a vented, overhead condenser system and a separator system for condensation of vaporized reactor material, separation of the condensed solvent therefrom, and reflux of separated solvent back into the reactor. The improvement comprises combining the reactor liquid feedstream with the refluxed solvent upstream from the oxidation reactor.

7 Claims, 2 Drawing Sheets

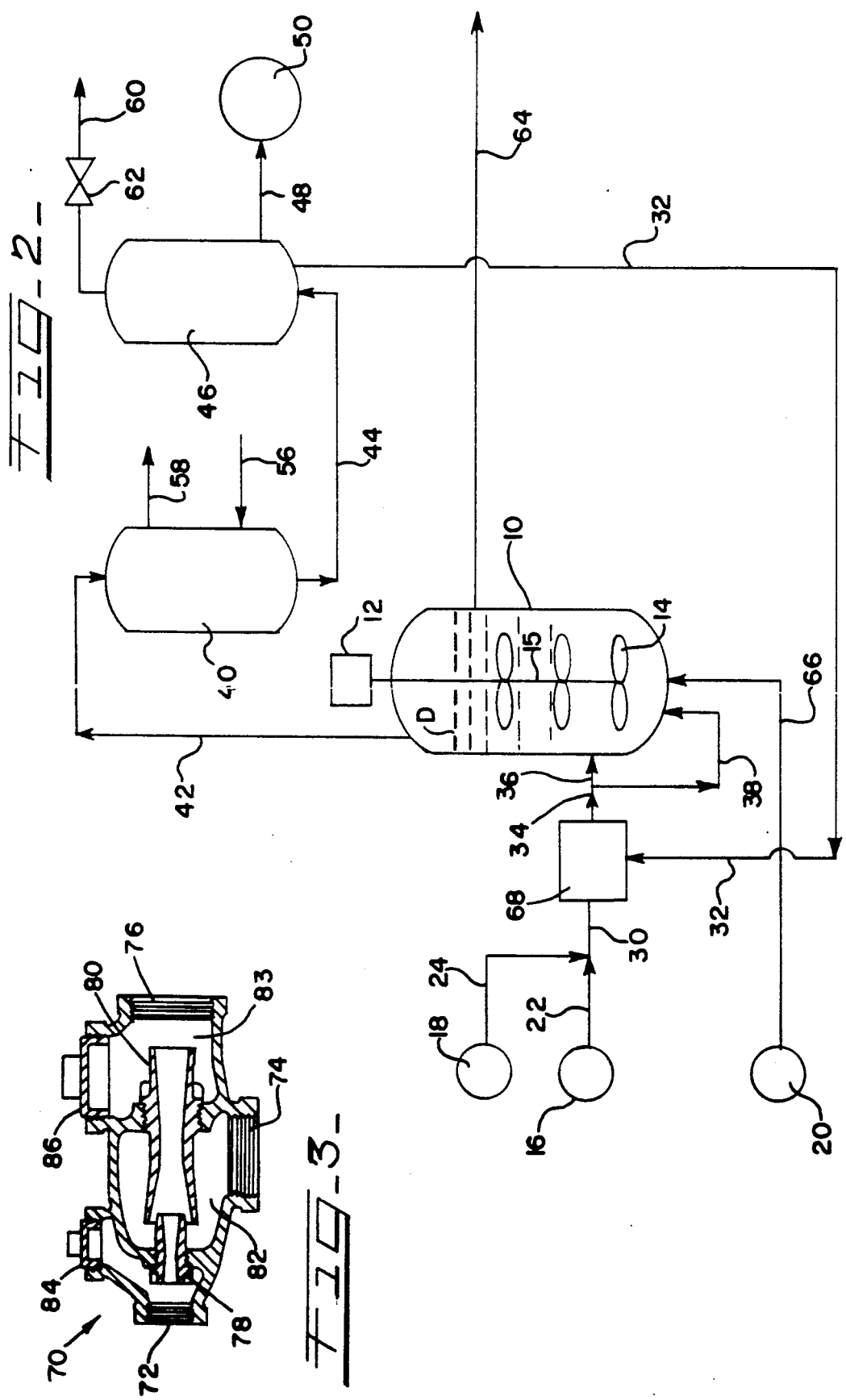

METHOD FOR INCREASING CONVERSION EFFICIENCY FOR OXIDATION OF AN ALKYL AROMATIC COMPOUND TO AN AROMATIC CARBOXYLIC ACID

FIELD OF THE INVENTION

This invention relates generally to the continuous, liquid phase oxidation of an aromatic alkyl to an aromatic carboxylic acid. More particularly, the present invention concerns a method and system for increasing reactor conversion efficiency and for improving the aromatic carboxylic acid product quality as well.

BACKGROUND OF THE INVENTION

Liquid phase oxidation of an aromatic alkyl to an aromatic carboxylic acid is a highly exothermic chemical reaction. Volatilizable aqueous acidic solvents are used to contain the reaction mixture and to dissipate the heat of reaction. Conventionally, the oxidation of aromatic alkyls in the liquid phase to form aromatic carboxylic acids is generally performed in a vented, well-mixed oxidation reactor, with a substantial portion of the heat generated by the exothermic oxidation reaction being removed by evaporating directly from the reaction mixture a portion of the aqueous solvent and aromatic alkyl contained within the reactor.

The materials vaporized as a result of the heat generated in the exothermic reaction, together with unreacted oxygen and other aqueous components that may be present, pass upwardly through the reactor and are withdrawn from the reactor at a point above the reaction mixture liquid level for the reactor. The vapors are passed upwardly and out of the reactor to an overhead reflux condenser system where the vaporized solvent, water and aromatic alkyl are condensed. The resultant condensate is thereafter separated, e.g., in a reflux splitter, into a portion having a relatively higher water concentration and a portion having a relatively lower water concentration. The separated portion having a relatively lower water concentration, now at a temperature less than the reactor contents' temperature, is refluxed back into the reactor by gravity. Conventionally, the refluxed portion of the condensate is returned directly to the reactor through a process line external to the reactor. The non-condensable gases, carried along with the vaporized reactor material, are vented.

In operation, the reactor is fed by a liquid feed stream containing the aromatic alkyl, aqueous acidic solvent and an oxidation catalyst. An oxygen-containing gas is separately introduced into the reactor for oxidizing the aromatic alkyl to the aromatic carboxylic acid in the presence of the catalyst.

The reaction mixture contained in the reactor typically comprises a suspension of crystalline aromatic carboxylic acid in liquid, volatilizable, aqueous acidic solvent as mother liquor. The mother liquor contains, in addition to dissolved catalyst, some dissolved aromatic carboxylic acid product and lesser amounts of partially-converted species of such product. The mother liquor can also include a minor amount of unreacted, aromatic alkyl.

Aromatic carboxylic acid product quality is measured by optical density. At present, optical density of the obtained product limits the oxidation reactor operating temperature and pressure, as well as the reactor throughput and mother liquor recycle rate into the reactor. Because of the commercial importance of the oxidation of aromatic alkyls, however, it is highly desirable to improve the reactor conversion efficiency and quality of aromatic carboxylic acids produced by the oxidation of aromatic alkyls.

The invention disclosed herein tends to diminish so-called reactor "entrance" effects, thought to be caused by an oxygen deficiency at the point where the reactor feedstream feeds the reactor. The invention disclosed herein also tends to minimize color-body generation, known to limit aromatic carboxylic acid plant operating flexibility and capacity.

SUMMARY OF THE INVENTION

The present invention is an improvement in a method and in a system for the continuous production of an aromatic carboxylic acid by liquid phase oxidation of an aromatic alkyl in an oxydation reactor. The improvement includes combining upstream from the reactor a liquid feed stream, containing an aromatic alkyl, with condensed acidic solvent medium that is refluxed back into the reactor, thereby providing a reflux-containing feed mixture, and then introducing the reflux-containing feed mixture into the oxidation reactor. A system embodying the present invention includes a liquid-liquid mixing means for effecting the "combining" step.

BRIEF DESCRIPTION OF THE DRAWINGS

FIG. 2 is a schematic process flow diagram of another embodiment of the present invention; and FIG. 3 is a detail on an enlarged scale showing a preferred liquid-liquid mixing means.

Figure 1:
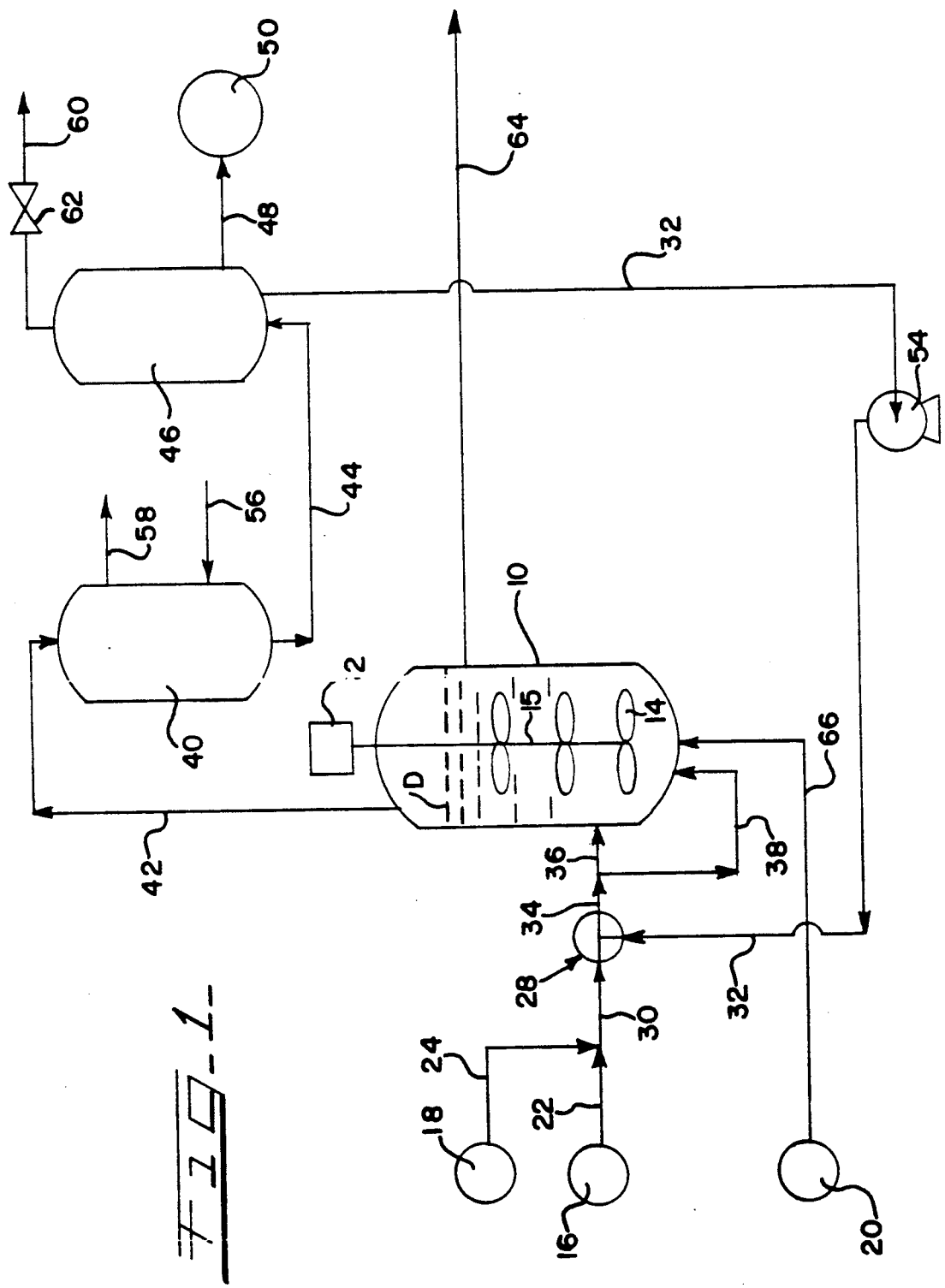
FIG. 1 is a schematic process flow diagram of one embodiment of the present invention.

The drawings of FIGS. 1 and 2, being process flow diagrams, are mere schematic illustrations. Accordingly, details which are not necessary for an understanding of the present invention have been omitted.

DETAILED DESCRIPTION OF PREFERRED EMBODIMENTS

Aromatic carboxylic acid is produced in an oxidation reactor at an elevated temperature and pressure by liquid phase, exothermic oxidation of an aromatic alkyl by an oxygen-containing gas in a vaporizable, aqueous acidic solvent medium. Oxidation of the aromatic alkyl to the aromatic carboxylic acid takes place in the aqueous acidic solvent medium in the presence of an oxidation catalyst. The conversion of aromatic alkyl to aromatic carboxylic acid is exothermic. Heat generated in the oxidation reaction is at least partially dissipated by vaporization of a portion of the solvent, water, aromatic alkyl and other vaporizable constituents of the reaction mixture present in the oxidation reactor. Vaporized reaction mixture constituents are withdrawn from the oxidation reactor, condensed in an overhead condenser system, and separated in a reflux splitter or a similar device into condensate portions having different water concentrations. Condensate portion having a relatively lower water concentration, and thus a relatively higher acidic solvent concentration, is fed back into the oxidation reactor.

A liquid feedstream for the oxidation reactor contains the aromatic alkyl, the acidic solvent medium, and an effective amount of an oxidation catalyst for effecting in the reactor a liquid phase oxidation of the aromatic alkyl, in the presence of oxygen, to the aromatic carboxylic acid. The improvement of the present invention comprises combining the refluxed condensate portion with the oxidation reactor liquid feed stream upstream from the oxidation reactor to produce a reflux-containing liquid feed mixture which is at a temperature below the reactor contents' temperature. The reflux-containing feed mixture is then introduced into the oxidation reactor.

Referring to FIG. 1, an elongated, vertically-disposed, continuous stirred-tank oxidation reactor 10 for oxidizing an aromatic alkyl to an aromatic carboxylic acid is shown. The oxidation reaction is continuous and proceeds in the liquid phase. The reactor 10 includes an agitator 12 which drives impeller blades 14, fixed to an agitator shaft 15. The reactor 10 further includes internal baffles (not shown). Each impeller blade 14 is rotated by the shaft 15 in a generally horizontal plane at a pre-selected rotational speed so that the contents of the reactor 10 are well mixed.

The contents of the reactor 10 are subjected to an elevated pressure and temperature sufficient to maintain the contained volatilizable solvent and aromatic alkyl substantially in the liquid state.

An aromatic alkyl, such as para-xylene, from a source 16, and a volatilizable aqueous acidic solvent medium, such as a catalyst-containing aqueous acetic acid solution, from a source 18, are combined to form a mixture. A liquid, reactor reflux stream from reflux splitter 48, contained in transfer pipe 32 and having a relatively higher acetic acid concentration than the non-refluxed condensate portion exiting via discharge pipe 48, is further combined with the formed mixture and is introduced into the reactor 10, via side inlet 36, as will be described in greater detail below. An oxygen-containing gas from a source 20 is introduced into the bottom of the reactor 10 via a gas inlet line 66. The oxygen-containing gas serves to oxidize the aromatic alkyl to an aromatic carboxylic acid in the presence of the catalyst.

Localized pockets of relatively low oxygen concentration or relatively high aromatic alkyl or catalyst concentration, such as are in the vicinity of the reactor inlet or the reactor baffles, are thought to reduce conversion efficiency of aromatic alkyl to aromatic carboxylic acid. To counteract these so-called "entrance" and "other" effects, it has been discovered that, when the reactor feed stream containing the aromatic alkyl and the volatilizable aqueous acidic solvent medium (the solvent medium containing the oxidation catalyst) is combined with the liquid reactor reflux stream to produce a reflux-containing mixture and the reflux-containing mixture is then introduced into the reactor 10, the overall conversion efficiency of aromatic alkyl to aromatic carboxylic acid is increased and the product quality is improved as well.

The prior art teaches recycling the reflux stream to the bottom of the reactor 10 and introducing the feed-stream into the side of the reactor 10. The present invention, however, contemplates introducing the combined reflux-containing liquid feed mixture either at the bottom or the side of the reactor 10, as desired.

Accordingly, in one embodiment of this invention, a liquid-liquid mixing means, such as the piping "T" connection 28 (FIG. 1), is provided. The aromatic alkyl is supplied to the "T" connection 28 by an inlet pipe 30 which carries the aromatic alkyl feed stream from source 16 via pipe 22 and the aqueous acidic solvent (containing the oxidation catalyst) from source 18 via pipe 24. The aromatic alkyl and aqueous acidic solvent mixture is further combined with the reactor reflux stream in "T" connection 28, with the reflux stream being introduced into "T" connection 28 by transfer pipe 32. The resultant reflux-containing reactor feed exiting the "T" connection 28 is transferred via discharge pipe 34 into the reactor 10 either at side inlet 36, bottom inlet 38, or both, as desired. The reactor side-inlet 36 is located below the reactor liquid level D. The temperature of the reflux-containing feed mixture is less than the reactor temperature.

The source of oxygen for the oxidation of this invention can vary. Air and oxygen-enriched gas such as oxygen-enriched air or gaseous oxygen can be used. The oxygen-containing gas, from whatever source, supplied to the reactor 10 provides sufficient oxygen to result in an exhaust gas-vapor mixture containing from about two to about eight volume percent oxygen (measured on a solvent-free basis) when the oxidation reactor is in operation. For example, when each alkyl substituent on the aromatic ring of the aromatic alkyl is a methyl group, a feed rate of the oxygen-containing gas sufficient to provide oxygen in the amount of from about 1.4 to about 2.8 moles per methyl group will provide such two to eight volume percent oxygen concentration in the gas-vapor mixture in the condenser 40.

In operation, the minimum pressure at which the reactor 10 is maintained is that pressure which will maintain a substantial amount of the aromatic alkyl present in the liquid phase and at least about 70 percent of the volatilizable, aqueous acidic solvent in the liquid phase. When the aqueous acidic solvent is an acetic acid-water mixture, suitable gauge pressures in the reactor 10 can be up to about 35 $kg/cm^2$ and typically are in the range of about 10 $kg/cm^2$ to about 30 $kg/cm^2$.

The process temperature employed is, on the one hand, low enough that the oxidation occurs with relatively low heat losses but, on the other hand, is high enough so that an economically desirable degree of conversion of the aromatic alkyl to the corresponding aromatic carboxylic acid is obtained. Process temperatures suitable for use in practicing the method of this invention generally are in the range of about 120° C. to about 240° C., preferably about 150° C. to about 230° C. Various narrower ranges may be preferred for a particular aromatic alkyl being oxidized. For example, when the aromatic alkyl is para-xylene, the preferred overall temperature range within the reactor 10 is about 175° C. to about 225° C., and the preferred temperature of the reflux-containing liquid feed mixture is about 85° C.

The residence time of the reactor is defined as the quotient of the reactor liquid volume divided by the liquid feed-stream flow rate into the reactor 10. Typically, in a commercial operation, the residence time in the reactor 10 is in the range of about 20 to about 90 minutes.

Suitable aromatic alkyls for use in the method of this invention include toluene, ortho-, meta-, and para-xylene, and the trimethylbenzenes. The respective aromatic carboxylic acid products are benzoic acid, orthophthalic acid, isophthalic acid, terephthalic acid, and the benzenetricarboxylic acids. Preferably, the method of this invention is used to produce terephthalic acid, isophthalic acid, and trimellitic acid (1, 2, 4-benzenetricarboxylic acid). More preferably, the method of this invention is used to produce terephthalic acid.

Suitable volatilizable, aqueous acidic solvents for use in the method of this invention can be aqueous solutions of any $C_2$–$C_6$ fatty acid such as acetic acid, propionic acid, n-butyric acid, isobutyric acid, n-valeric acid, trimethylacetic acid, caproic acid, and mixtures thereof.

The volatilizable acidic solvent preferably is aqueous acetic acid. When combined with the liquid feed, the volatilizable aqueous solvent preferably contains from about 0.5 to about 20 weight percent of water. However, after being combined with the reflux stream, the resultant reflux-containing liquid feed fed to reactor 10 can contain up to about 35 weight percent of water.

Suitable catalysts for present purposes include any catalyst system conventionally used for liquid phase oxidation of an aromatic alkyl. A suitable catalyst system preferably includes a mixture of cobalt, manganese and bromine compounds or complexes, that are soluble in the particular volatilizable, aqueous acidic solvent employed. When the catalyst system comprises soluble forms of cobalt, manganese or bromine, the cobalt (calculated as elemental cobalt) preferably is present in the range about 0.1 to about 10.0 milligram atoms (mga) per gram mole of the aromatic alkyl. Similarly, the manganese (calculated as elemental manganese) is preferably present in the ratio of about 0.1 to about 10.0 mga per mga of the cobalt. Further, the bromine (calculated as elemental bromine) is preferably present in the ratio of from about 0.2 to about 1.5 mga per mga of total cobalt and manganese (both on an elemental basis).

In the method and system embodiments of this invention in which the catalyst system employed comprises a mixture of soluble forms of cobalt, manganese and bromine, and the solvent is aqueous acetic acid, each of cobalt and manganese can be provided in any of its known ionic or combined forms that are soluble in aqueous acetic acid solutions. For example, such forms can include cobalt and/or manganese carbonate, acetate tetrahydrate, and/or bromide. However, the desired catalysis cannot be effected by bromides of both cobalt and manganese. Rather, the catalysis can be effected by appropriate ratios of the bromide salts and other aqueous acetic acid-soluble forms containing no bromide; for example, the acetates. As a practical matter, and by way of non-limiting example, a 0.1:1 to 10:1 ratio of manganese mga to cobalt mga is provided through use of the aqueous, acetic acid-soluble forms other than bromides; for example, both as acetate tetrahydrates. A 0.2:1 to 1.5:1 ratio of elemental bromine mga to total cobalt and manganese mga is provided by a source of bromine. Such bromine sources include elemental bromine ($Br_2$), and ionic bromides (for example, HBr, NaBr, KBr, $NH_4Br$, etc.).

Heat of reaction in the reactor 10 vaporizes the volatilizable solvent, water and reaction mixture contained therein. A substantial portion of the heat generated by the exothermic reaction in the reactor 10 is removed from the reaction mixture by vaporization of the aqueous solvent and, to a lesser extent, the aromatic alkyl. The vaporized material and any unreacted oxygen and other components of the oxygen-containing gas fed to the reactor 10 pass upwardly through the reactor 10 and are withdrawn from the reactor 10 via the exit pipe 42. The vaporized materials contained within pipe 42 are received into an overhead condenser system such as the condenser 40, are condensed, and are conveyed by a transfer line 44 into a reflux splitter 46 in which the condensed solvent phase is separated into two portions having different acid, and thus water, concentrations. Such liquid-liquid splitters are well-known in the art and will not be described herein. (See, e.g., *Perry's Chemical Engineers' Handbook*, 6th Ed., published 1984 by McGraw-Hill, at pages 21-64 through 21-83.)

The amount of acidic solvent contained in the refluxed portion of the condensed solvent, being dictated by the operation of the reflux splitter 46 and the overall plant economics, of course, can vary. However, a major portion of the water produced by the liquid phase oxidation of the aromatic alkyl is removed in the non-refluxed portion of the condensate in reflux splitter 46 via discharge pipe 48 from the reflux splitter 46 to storage means 50 for further use, or to waste, as desired. The non-refluxed portion of the condensate contains water, a relatively lower concentration of aromatic carboxylic acid, and a minor amount of aromatic alkyl.

The refluxed portion of the condensate from the reflux splitter 46, containing aromatic alkyl, water, a relatively higher acidic solvent concentration, and aromatic carboxylic acid, is returned from reflux splitter 46 into reactor 10 via transfer line 32, and is combined with the aromatic alkyl in the "T" connection 28, as described above. A pump 54 can be used to assist flow of reflux through line 32 into the "T" connection 28, if desired. In this manner, localized oxygen starvation in pockets of high aromatic alkyl and catalyst concentrations within the reactor 10 is avoided.

To effect condensation, coolant is introduced into the condenser 40 through coolant inlet pipe 56 and exits via coolant discharge pipe 58. The condensate from condenser 40 flows generally downwardly and through transfer line 44, and upwardly into the splitter 46. Noncondensable gases, included with the vaporized reactor material introduced into the condenser 40, are vented from the separator 46 through a vent pipe 60 which includes a flow-control valve 62. Preferably, the oxygen concentration from the vent gas is about three to about four percent oxygen by volume, but can be in the overall range of about two to about eight percent oxygen by volume.

The reaction mixture, which typically comprises a suspension of crystalline aromatic carboxylic acid in liquid, volatilizable, aqueous acidic solvent mother liquor, is conventionally transferred by a discharge pipe 64 to suitable crystallizers (not shown). The discharge pipe 64 is located below the reactor liquid level D. The reactor feed pipe 36 is preferably located on the reactor 10 lower than the reactor discharge pipe 64 and is spaced about 180 degrees therefrom to minimize the likelihood of any aromatic alkyl, introduced by inlet 36, being in the reactor 10 for less than the desired residence time.

In the reactor 10, the aromatic alkyl is oxidized by oxygen, usually introduced as air at the bottom of reactor 10 by inlet pipe 66, in the presence of the catalyst, to form the desired aromatic carboxylic acid and intermediates thereto. A product stream is withdrawn as an effluent stream from the reactor 10 via the discharge pipe 64. The product stream is thereafter treated using conventional techniques to separate its components and to recover the aromatic carboxylic acid contained therein, usually by crystallization.

A further embodiment of the present invention is illustrated in FIG. 2. As between FIGS. 1 and 2, like reference numerals have been assigned to like parts or elements of the present invention. Further, for the sake of brevity, and because the function of many of the parts or elements appearing in FIG. 2 have been described in connection with FIG. 1, only those parts or elements of FIG. 2 which have not been discussed heretofore will be discussed at length hereinbelow.

As shown in FIG. 2, a liquid-liquid mixing means 68 is used to combine the aromatic alkyl and aqueous acidic solvent from line 30 with the reflux from line 32 to provide the reflux-containing liquid feed mixture to be fed via side-inlet line 36 or bottom-inlet line 38 into the reactor 10. Such a liquid-liquid mixing means can be a so-called "static" mixer or any one of a large number of other flow or line mixers well-known in the art. (See, e.g., *Perry's Chemical Engineers' Handbook*, 6th Ed., at pages 21-57 through 21-64.) Preferably, the choice of a liquid-liquid mixing means 68 is such that it does not require the use of a pump such as the optional pump 54 in transfer pipe line 32.

Such liquid-liquid mixing means can be a liquid-handling device conventionally referred to as a jet pump. A jet pump is a suitable liquid-handling device which makes use of the momentum of one fluid to move another. The preferred liquid-liquid mixing means, shown in FIG. 3, is a liquid-liquid ejector 70, a type of jet pump which is well-known in the art.

The liquid-liquid ejector 70 shown in FIG. 3 includes an aromatic alkyl and aqueous solvent mixture inlet port 72, a reactor reflux suction port 74 and a discharge port 76. Fluid momentum originating at the sources 16 and/or 18 forces the aromatic alkyl and aqueous solvent mixture into and through the first venturi 78 which feeds the second venturi 80 thereby creating suction at suction port 74 and causing the reactor reflux stream to enter the suction port 74 and flow into the ejector fluid suction chamber 82. From the suction chamber 82 the reflux stream enters the fluid-mixing chamber 83 where the liquid-phase solvent reflux is combined and mixes with the mixture of aromatic alkyl and aqueous acidic solvent. The fluid momentum provided at sources 16 and 18 usually is sufficient to discharge the resultant mixture from the liquid-liquid ejector 70 via discharge port 76 and through side inlet 36 or bottom inlet 38 into the reactor 10, as desired. To facilitate clean-out of the liquid-liquid ejector 70, first and second threaded clean-out plugs 84 and 86 are provided.

Combining the reactor-reflux stream with the reactor-feed stream increases the ratio of acidic solvent to aromatic alkyl in the resulting combined feed stream. It has been found that this tends to increase overall conversion efficiency of aromatic alkyl to aromatic carboxyl acid as well. The prior art method of recycling reflux from the reflux splitter 46 into the reactor 10 teaches introducing the reactor feed stream (containing the aromatic alkyl and aqueous solvent) at a reactor location point spaced from the reflux return point. When the aromatic alkyl is para-xylene and the aqueous solvent is aqueous acetic acid, the ratio of acetic acid to para-xylene in the reactor feed under the prior art scheme is about 3:1 (volumetric basis). In contradistinction, when the aromatic alkyl and aqueous acidic solvent mixture is combined with the reactor reflux, as discussed above in connection with the present invention, the refluxed portion of the condensate has a relatively higher acetic acid concentration and the ratio of acetic acid to para-xylene in the resultant reactor feed stream is about 14:1 (volumetric basis).

The foregoing description exemplifies preferred embodiments of the present invention. Still other variations and rearrangements of component parts are possible without departing from the spirit and scope of this invention and will readily present themselves to one skilled in the art.

What is claimed is:

1. In a method for the continuous production of an aromatic carboxylic acid product by the liquid phase, exothermic oxidation of an aromatic alkyl with an oxygen-containing gas and aqueous acidic solvent medium present in an oxidation reactor and in the presence of an oxidation catalyst, wherein heat generated in the oxidation reactor is at least partially dissipated by vaporization of the aqueous solvent medium therein, the vaporized aqueous acidic solvent medium is withdrawn from the oxidation reactor and condensed in a reflux condenser system, the improvement which comprises:

providing a liquid feedstream for the oxidation reactor, the liquid feedstream containing the aromatic alkyl and the aqueous acidic solvent medium;

combining a separated portion of the condensed solvent medium having relatively lower water content with the liquid feedstream, thereby providing a solvent reflux-containing feed mixture; and introducing the solvent reflux-containing feed mixture into the oxidation reactor.

2. The method in accordance with claim 1 wherein the aromatic carboxylic acid is terephthalic acid, isophthalic acid or trimellitic acid.

3. The method in accordance with claim 1 wherein the aromatic alkyl is para-xylene and wherein the aromatic carboxylic acid is terephthalic acid.

4. The method in accordance with claim 3 wherein the aqueous acidic solvent medium and the condensed solvent are aqueous acetic acid and the portion of the condensed aqueous solvent medium refluxed to the reactor contains a relatively higher concentration of acetic acid than the portion of the condensed aqueous solvent medium not refluxed.

5. The method in accordance with claim 4 wherein the volume ratio of acetic acid to para-xylene is about 3:1 in the liquid feedstream and is about 14:1 in the solvent reflux-containing feed mixture.

6. The method in accordance with claim 1 wherein the aqueous solvent medium and the condensed solvent phase are aqueous acetic acid and the portion of the condensed aqueous acidic solvent medium refluxed to the reactor contains a higher concentration of acetic acid than the portion of the condensed aqueous acidic solvent medium not refluxed.

7. The method in accordance with claim 1 wherein the solvent medium in the oxidation reaction is at a pre-selected temperature in the range of from about 120° C. to about 240° C. and wherein the solvent reflux-containing feed mixture is at a temperature less than the pre-selected temperature.

* * * * *